United States Patent
Nevo et al.

(12) 
(10) Patent No.: US 6,632,651 B1
(45) Date of Patent: Oct. 14, 2003

(54) TISSUE MAINTENANCE SYSTEM THAT APPLIES RHYTHMIC PULSES OF PRESSURE

(75) Inventors: Zvi Nevo, Herzliya (IL); Dror Robinson, Shimson (IL)

(73) Assignee: Ramot at Tel Aviv University Ltd., Ramot Aviv (IL)

( * ) Notice: Subject to any disclaimer, the term of this patent is extended or adjusted under 35 U.S.C. 154(b) by 0 days.

(21) Appl. No.: 09/345,138

(22) Filed: Jul. 6, 1999

(51) Int. Cl.$^7$ .............................. C12M 1/36; C12M 3/00; C12N 11/02; C12N 5/06; C12N 5/08
(52) U.S. Cl. .................... 435/286.5; 435/177; 435/395; 435/283.1; 435/284.1; 435/286.1; 435/289.1; 435/1.1
(58) Field of Search ................... 435/1.1, 174, 177, 435/180, 325, 395, 283.1, 284.1, 286.1, 286.5, 289.1

(56) References Cited

U.S. PATENT DOCUMENTS

| | | | |
|---|---|---|---|
| 4,851,354 A | 7/1989 | Winston et al. ............. 435/284 |
| 4,880,429 A | 11/1989 | Stone .......................... 623/18 |
| 5,108,438 A | 4/1992 | Stone .......................... 623/17 |
| 5,162,114 A | 11/1992 | Kuberasampath et al. .. 424/423 |
| 5,188,962 A | * | 2/1993 | Hasegawa et al. ........... 435/287 |
| 5,843,182 A | 12/1998 | Goldstein ...................... 623/2 |
| 6,037,141 A | 3/2000 | Banes .......................... 435/30 |

FOREIGN PATENT DOCUMENTS

| | | |
|---|---|---|
| DE | 19808055 | 9/1999 |
| WO | 9214419 | 9/1992 |
| WO | 9721447 | 6/1997 |
| WO | 9749799 | 12/1997 |
| WO | 9814222 | 4/1998 |
| WO | 9822573 | 5/1998 |
| WO | 9952572 | 10/1999 |
| WO | 0041648 | 7/2000 |

OTHER PUBLICATIONS

Mikos, A.G., et al. "Laminated three–dimensional biodegradable foams for use in tissue engineering" Biomaterials, vol. 14, No. 5, (1993).

Hutmacher, D., et al. "Matrix and Carrier materials for Bone GrowthFactors: State of . . . Perspective" Stark. G.B., et al. (Eds.) Biological Matrices and Tissue Reconstructions, p. 197–203, (1998).

Kandel, R.A., et al. "Transplantation of Cartilagenous Tissue Generated in vitro into Articular Joint Defects" Art. Cells, Blood Subs., and Immob. Biotech., vol. 23(5), p. 565–577, (1995).

* cited by examiner

Primary Examiner—David M. Naff
(74) Attorney, Agent, or Firm—Ladas & Parry

(57) ABSTRACT

A growth support scaffold for cells and tissue is formed of naturally derived connective or skeletal tissue which has been treated for elimination of cellular and cytosolic elements, and modified by cross-linking with hyaluronic acid, proteoglycans, glycosaminoglycans, chondroitin sulfates, heparan sulfates, heparins or dextran sulfates. The scaffold may contain cell adhesive molecules and growth factors, and can be formulated as a malleable prosthesis. A tissue maintenance system is provided containing a chamber having a constant atmosphere which may contain the scaffold impregnated with cells, a medium-containing reservoir, a pump which can be computer controlled for circulating the medium between the chamber and reservoir and may change direction of medium flow every 1 to 3 minutes, and a pressure generator, which can be the pump, for producing rhythmic pulses of pressure such as between 0.5 to 30 atm and frequency of 5–300 per minute.

10 Claims, 8 Drawing Sheets

TISSUE MAINTENANCE SYSTEM THAT APPLIES RHYTHMIC PULSES OF PRESSURE

FIELD OF THE INVENTION

The invention concerns scaffold matrixes for supporting three-dimensional tissues and systems for maintaining three-dimensional viable tissues.

BACKGROUND OF THE INVENTION

The following publications are believed to be relevant as background of the invention.

WO 98/22573
U.S. Pat. No. 4,880,429
U.S. Pat. No. 4,108,438
U.S. Pat. No. 5,843,182.

Cartilage is a specialized form of connective tissue composed of cells and matrix. The cartilage cells synthesize matrix and become encased in cavities (lacunae) within it. The matrix is composed of fibers embedded in ground substance and endows cartilage with its specialized physico-chemical properties.

Trauma, single or repetitive, is the most known cause of damage and degeneration of articular cartilage, that leads to pain, chronic disability and ultimately to joint failure. The current options for treatment provide temporary improvement of symptoms and function, however, there is no full restoration of joint performance. Prosthetic joint replacement is currently the ultimate and the most commonly employed treatment. Modem biological grafting is the other alternative for resurfacing the damaged joint, but is still imperfect.

A large number of candidate grafts have been studied for enhancing the repair of cartilage defects which include: (i) Osteochondral graft (autografts or allografts); (ii) Intact cartilage grafts; (iii) Growth plate; (iv) Isolated allogeneic chondrocytes; (v) Cultured autologous chondrocytes (dedifferentiated) (vi) Periosteum; (vii) Perichondrium; (viii) Bone marrow mesenchymal derived cells and (ix) Synovial membrane.

Another approach was the attempt to use natural occurring or synthetic biodegradable scaffolds which support three-dimensional growth of cartilage cells. The scaffolds may be impregnated with cells, which together with the scaffold form the graft. Alternatively, the scaffold may initially be devoid of impregnated cell, and endogenous cells from the patient are expected to migrate into the scaffold after its implantation.

Examples of such scaffolds are: (a) Fibrin polymers; (b) Collagent Type I; (c) Natural hyaluronic acid (HA) and chemically modified HA and (d) Synthetic bipolymers either biodegradable or non-biodegradable (e.g. alginic acid) and (e) Polylactic acid, polyglycolic acid. However, none of the above scaffolds can induce generation of hyaline-like cartilage. Fibrin polymers tend to induce dedifferentiation and thus do not permit production of functional tissue. Collagen Type I has no inherent chemotactic ability for chondrocytes, but stimulate proliferation of fibroblast. Thus instead of encouraging migration of chondrocytes the tissue formed in this scaffold tends to be fibrous. Hyaluronic acid can stimulate chondrogenic differentiation, but does not stimulate chondrocytes proliferation. Alginic acid is a foreign cabohydrate and thus might induce an antigenic reaction, and furthermore is not biodegradable. Polyglycolic and polylactic acid scaffolds do not support good hyaline cartilage regeneration due to acidic conditions during degradation.

Damaged or missing hyaline cartilage is frequently repaired by transplantation of homografts. Homografts are immunologically privileged the matrix acts as a barrier that permits only limited diffusion of high-molecular weight substances and contains an anti-angiogenesis factor to prevent invasion of host blood vessels and fibroblasts.

Various culturing systems have been developed for maintaining the viability and growth of tissues in culture. Generally, these are divided into static and perfusion bioreactors. Perfusion bioreactors are reactors which essentially keep constant, growth permissible conditions (such as gas composition, temperature, pH, etc.) in which the growth fluid medium is constantly perfused in and out of the system. Typically, perfusion is carried out by utilizing a constant velocity flow of the medium.

SUMMARY OF THE INVENTION

By a first aspect, the present invention concerns a scaffold for use as growth supportive base for cells and tissue explants from three-dimensional tissue, comprising naturally derived connective or skeletal tissue which has been treated for elimination of cellular and cytosolic elements, and which has been modified by cross-linking with an agent selected from the group consisting of: hyaluronic acid, proteoglycans, glycosaminoglycan, chondroitin sulfates, heparan sulfates, heparins and dextran sulfates.

It has been found that such a scaffold has the properties of encouraging cells adherence thereto and enablement of propagation of cells on the one hand, while the cross-linking with the agents specified above gives the scaffold mechanical strength, produces a substance which is less brittle with prolonged degradation time on the other hand. It was further found that the scaffold of the invention supports chondrocyte proliferation at the expense of fibroblasts, resulting in a hyaline-like repair tissue.

The term "scaffold" in the context of the present invention refers to the connective/skeletal tissue which has been treated for elimination of cellular and cytosolic agents and modified by cross-linking as described above, as well as to such a construct containing additional agents such as adhesive molecules or growth factors.

The term "three-dimensional tissue" (3D tissue) refers to any type of tissue which has an orderly three-dimensional structure, i.e., is not naturally present in the body in the form limited to a single layer of cells or lamina, but has a stucture which is spatially ordered. Examples of three-dimensional tissue are: mesenchymal tissue, cartilage and bone tissue, liver tissue, kidney tissue, neuronal tissue, fibrous tissue, dermis tissue etc. Another three-dimensional tissue is the whole embryonal epiphyseal organ derived from embryos at a post limb-bud stage.

The naturally derived connective or skeletal tissue is, in general, tissue that was derived from mesenchymal tissues that express, temporarily or continuously fibroblast growth factor receptor 3 (FGFR3). Examples of such tissue are mainly members of chondrogenic and osteogenic anlagen, as well as the residual mesenchymal stem cell reservoirs found in tissues all along life, ready to carry wound healing, repair and regeneration tasks. Another example of connective or skeletal tissue is epiphyseal tissue.

The tissue should be treated for elimination of cellular and cytosolic elements such as: DNA, RNA, proteins, lipids, proteoglycans and in general most elements of the cells which are immunogenic, as well as treated for removal of calcification-mineralization centers. Methods for elimination of the above cellular and cytosolic elements are in general known in the art.

The naturally derived connective or skeletal tissue treated as described above for elimination of cellular and cytosolic components is preferably further treated for producing porosity by the production of pores in a controlled manner. The treatment may be mechanical, for example, by hammering the tissue on a scraper device.

Alternatively, the treatment for producing porosity may be a chemical extraction process carried out by exposing the tissue, for a controlled amount of time, in a controlled environment to chemical agents capable of degradation of the tissue. In addition or alternatively, the treatment for producing porosity may be by exposing the tissue to enzymatic agents such as proteolytic enzymes, capable of partial degradation of the tissue. Example of such chemical agents which can produce pores in the tissue are guanidium chloride. The pores should have preferably a size of 10–500$\mu$, most preferably 20–100$\mu$.

The agents either specified in above (i.e. hyaluronic acid, proteoglycans, glycosaminoglycan, chondrotin sulfates, heparan sulfates, heparin and dextran sulfates) or additional agents such as adhesive molecules or growth factor moieties may be linked to the residual scaffold either by sugar cross-linking, (for example using ribose and xylose) or by carbodiimideor 1, 1 carbonyl di-imidazole. Cross-linking with the above agents is generally carried out as known in the art of coupling in organic chemistry.

In accordance with the present invention, it is preferable that the scaffold would also contain adhesive molecules in order to enhance cell adherance to the scaffold. Example of suitable adhesive molecules are the integrins and additional agents such as, laminin, fibronectin, hyaluronic acid, polylysine and lysozyme.

In accordance with the present invention, it is also preferable that the scaffold would contain growth factors, in order to enhance the rate of growth of the cells filling the three-dimensional space of the scaffold. Examples of suitable growth factors are: fibroblast growth factors (FGF's), TGF's, BTP's, IGF's. The growth factor chosen should depend on the type of tissue used.

As indicated above, the adhesive molecules and growth factor molecules should be made part of the scaffold by cross-linking as explained above.

By one option, it is possible to formulate a prosthesis from the scaffold alone, i.e. of a scaffold devoid of cells. In such a case, the scaffold is formulated to a desired shape and is inserted into the desired location in the body of the individual, for example, a location wherein it is desired to achieve invasion of endogenous mesenchymal cells such as in the knee joint.

The prosthesis is maleable and can be shaped as either a flat sheet of several millimeters in thickness or any other three-dimensional shape adapted to the shape of the lesion. Alternatively, the prosthesis, can, a priori, prior to implantation contain embedded (impregnated) cells or tissue explants to allow their fast anchorage and integration into bone and cartilages.

The cells impregnating the prosthesis should preferably be from an autogeneic source, but can also be of an allogeneic source, as cartilage has a sort of an immunoprivilage.

The scaffold of the invention impregnated with cells may be used, not only for implanting in the body but also for prolonged in vitro growth and differentiation of various three-dimensional tissues kinds such as skin, neuronal, bony, cartilaginous, liver, pancreatic beta cell and almost of any organ or tissue in a bioreactor, while adjusting the proper medium, coctail of growth factors and adhesive molecules.

By another aspect the present invention concerns a system for maintaining viable three-dimensional tissue. In accordance with this second aspect, it was surprisingly found that for long-term maintenance of viable three-dimensional tissue, there is need to apply rhythmic pulses of pressure (hydrostatic, mechanical or shear force) in order to obtain optimal growth. For example for growing of an articular cartilage tissue there is an advantage in maintaining the tissue under reparative cycles of loads and unloads of pressure in a rhythmic manner, simulating the natural growth conditions in the joint. The cellular mechanoreceptors seem to play a key role in this respect of cell growth.

The variables that can be manipulated in the system of the invention include stream flow velocity, amount (in atmospheres) of hydrostatic and/or mechanic pressure, rhythmic action periods (frequency of applications of pressure) and pausal intervals as well as change stream direction of the medium. By this second aspect, the present invention concerns a system for the maintenance of viable tissue comprising;

(i) a chamber for holding the tissue, the chamber's atmosphere being kept at a relatively constant gas composition, said gas composition being suitable for maintenance of viable biological tissues;

(ii) a reservoir for holding tissue culture medium, said reservoir being in flow communication with the chamber;

(iii) a pump for circulating the medium between the chamber and the reservoir in a controlled manner; and (iv) a pressure generator for producing rhythmic pulses of pressure on the tissue present in the chamber.

The system of the invention is suitable for any type of cells or tissues, but is especially suitable for the growth of a three-dimensional tissue, according to the definition above.

Basically, the system comprises a chamber for holding the tissue, the chamber's atmosphere being kept at relatively constant gas and temperature composition which are suitable for maintenance of viable biological tissue, for example 5% to 10% $CO_2$ in air at physiological temperature. This is usually achieved by placing the chamber within a larger $CO_2$ incubator, capable of maintaining such an atmosphere, and ensuring that the atmosphere of the incubator in communication (as regards temperature and gas composition) with that of the chamber.

The system further comprises a reservoir for holding tissue culture medium which is in flow communication with the chamber. Preferably, the size of the reservoir is about 30 to 100 larger than that of the chamber for holding the tissue and is typically the size of 400–1000 ml. The medium in the reservoir of course contains the nutrients and various agents such as growth factors, etc. required for maintaining viability and growth of the tissue.

The system comprises a pump which circulates the growth medium between the chamber and the reservoir in a controlled manner. The pump may be a constant pump or a peristaltic pump utilizing computerized manipulated regimes, as will be explained hereinbelow. Typically, the velocity of medium flow is in the range of 300–600 ml/min.

The pressure generator may produce mechanical or hydrostatic pressure on the tissue and may be, for example, a compressor present in the chamber, which can periodically apply pressure on the tissue present in the chamber when streaming in one direction and the pressure is released when streaming in the other direction. The compressor should be under control of a control mechanism capable of controlling the timing (frequency, pausal, etc.) and level of compression, such as a clock or a computer mechanism.

The control mechanism would trigger the compressor, to compress the chamber thus applying rhythmic pressure on the liquid present therein, and consequently applying pressure on the tissue. In the case of a compressor, the pump's activity may be constant so that the medium circulates between the chamber and the reservoir at a constant rate in order to improve gas exchange and nutrient availability to the tissue.

By another alternative, the pump that circulates the medium between the chamber and the reservoir is itself the pressure generator capable of producing rhythmic pulses of hydrostatic pressure on the tissue. In that case the pressure generator is the pump itself and no additional elements (such as a compressor) are required to produce the rhythmic pulses of pressure. The pump which is a perstaltic may have a built-in means for triggering rhythmic pulses. Alternatively, the pump may be connected to a control mechanism which triggers the duration, delays and frequencies of the pump such as a clock or a computer mechanism.

By alternating activities of such a pump, the medium can circulate in pulses between the medium reservoir and the chamber, thus creating rhythmic pressure pulses on the tissue. Preferably the direction of the medium flow should be changed (for example clock-wise and then counter-clockwise) as changing the flow direction simulates best the joint's conditions of loading and unloading. Typically change of direction should be every 1 to 3 min.

The rhythmic pulses should have a frequency of 5–300 per min., preferably 10–200 per min., most preferably 60 to 120 per min.

The hydrostatic pressure should be between 0.5 and 30 atm., preferably 1 to 10 atm, most preferably 2 to 3 atm.

The present invention concerns a method for maintaining viable tissue, cells or extracts from three-dimensional tissue, comprising placing these tissues in the chamber of the above system with any of the above parameters of pressure, frequency and change of flow direction. Examples of tissue are as defined above in connection with the scaffold.

The present invention further provides a method for maintaining viable cells or tissue extracts from three-dimensional tissue comprising growing a prosthesis composed of the scaffold of the invention impregnated with cells in the system of the invention with conditions specified above (i.e. the parameters specified above). A preferable example is a method for growing epiphyseal tissue.

DETAILED DESCRIPTION OF THE INVENTION

Figure 1:
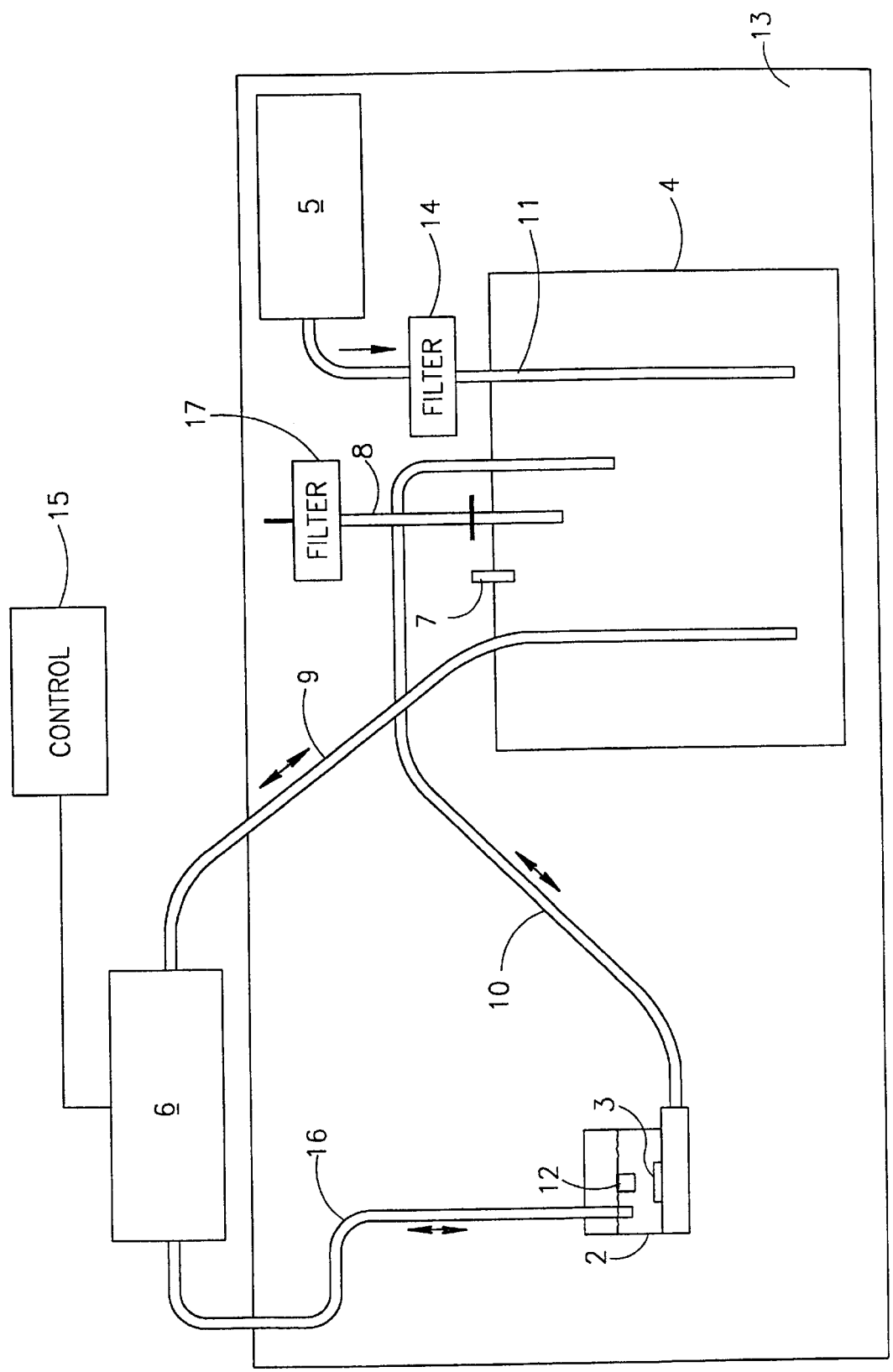
FIG. 1 shows a schematic representation of the system of the invention for maintaining viable three-dimensional tissue.

Reference is now made to FIG. 1 which shows an embodiment of the system of the invention 1. The system is composed generally of a chamber 2 which holds within scaffold 3 of the invention impregnated with cells, for example epiphyseal tissue. The system further comprises a medium-containing reservoir 4 which is filled with a media capable of supporting and maintaining viable cells. Medium flows from chamber 4 through out flow tube 9 into pump 6 and then through tube 16 into chamber 2. The medium then returns to the reservoir through connecting chamber outflow tube 10. The circulation of the medium is mediated through pump 6. In the present example, the pump is the element creating rhythmic pressure by its rhythmic activities and is a peristaltic pump. By other examples the pump may work continuously and rhythmic pressure may be created by other independent means such as a compressor.

The chamber and the reservoir are enclosed in $CO_2$ equilibrium incubator 13, which maintains constant gas contact and temperature. In reservoir 4, there is a small aquarium pump 5 and filter 14 for circulating the medium in the reservoir, filtering out particles and contaminates. The reservoir also includes needle valve 8 to equilibrate and release pressure, as well as gases outlet 11. Chamber 2 includes a mechanical plunger 12.

The system also comprises control mechanism 15 which in this case is a computer. The computer controls the timing, duration, pausing of the activity of pump 6 as well as the direction of the flow in the system. Thus, by giving the computer correct parameters, it is possible to activate pump 6 rhythmically so that it can work and pause alternatively resulting in streaming which will cause hydrostatic pressure on the cells present in scaffold 3 in chamber 2. Furthermore, by this control the pump may change the direction of the flow of medium. It may initially flow in the direction of 4→9-6→16-2→10→4, and then the direction may be reversed so that it flows in the reverse direction.

The volume of reservoir chamber 4 is preferably about 50 times that of chamber 2.

The chamber 2 and the medium reservoir 4 are enclosed in an incubator 13 at 37° C. and a pH of 7.25±0.05.

EXAMPLE 1

Tissue Maintenance in the System of the Invention

Maintenance of whole embryonal epiphyses (an avian model) both as a separated organ, several epiphyses fused together was determined in the system of the invention. Whole epiphyses used further as implants transplanted by squeezing them into articular defects.

Maintenance was achieved by keeping the epiphyses in the device shown in FIG. 1 for 10–20 days. Vitality was assessed by histology $^{35}$S-sulfate incorporation into isolated glycosaminoglycans and by XTT test (as explained below in Example 6). The results are shown in FIGS. 2(a) and (b).

Figure 2A:
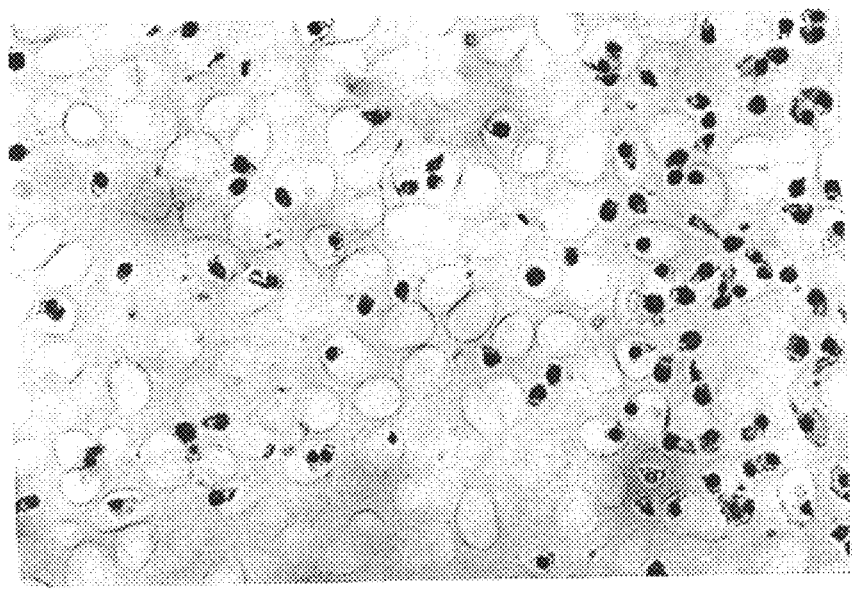
FIG. 2(a) shows a histological section from whole embryonal epiphyses maintained under static growth conditions in a growth medium.
Figure 2B:
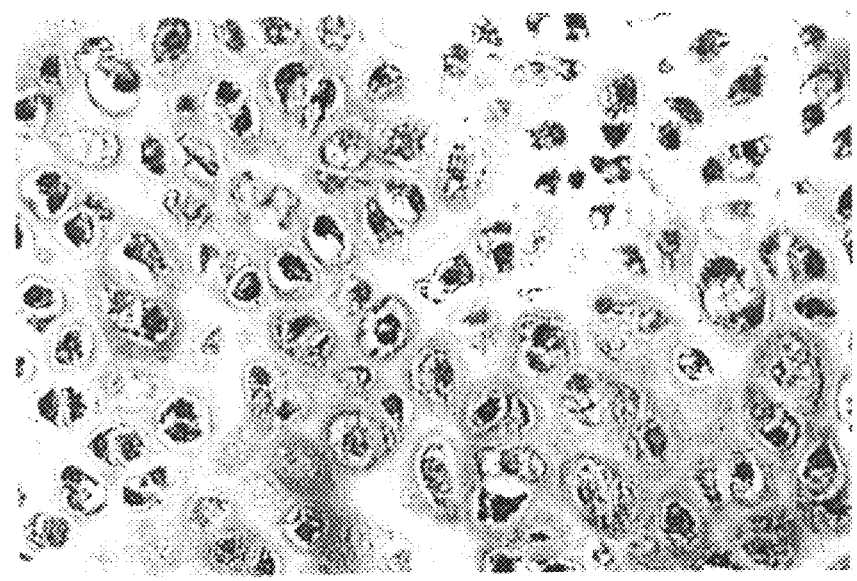
FIG. 2(b) shows histological sections from whole embryonal epiphyses maintained in the system of the invention under conditions of rhythmic pressure.
Figure 3A:
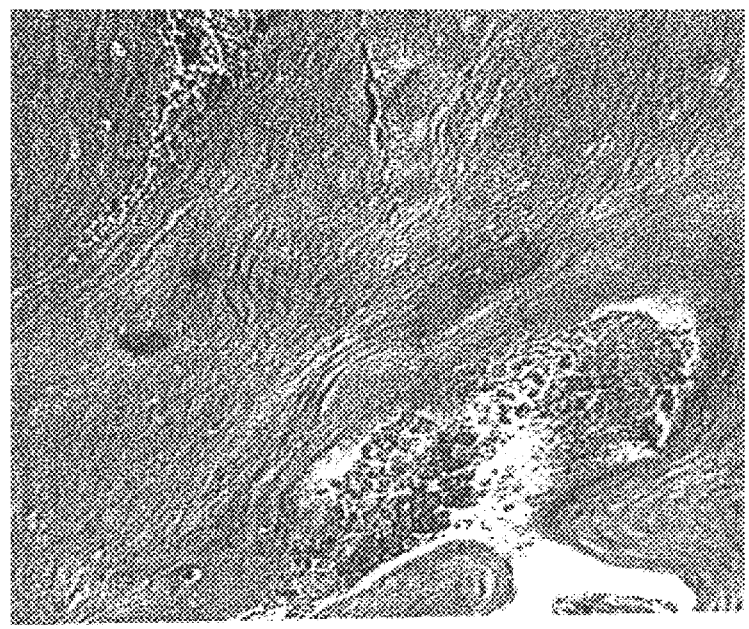
FIGS. 3(a)–(d) shows histological cross-sections of scaffolds of the invention composed of demineralized cortical and spongious bovine bone modified by cross-linking, which is impregnated with human chondrocytes.
Figure 3B:
Figure 3C:
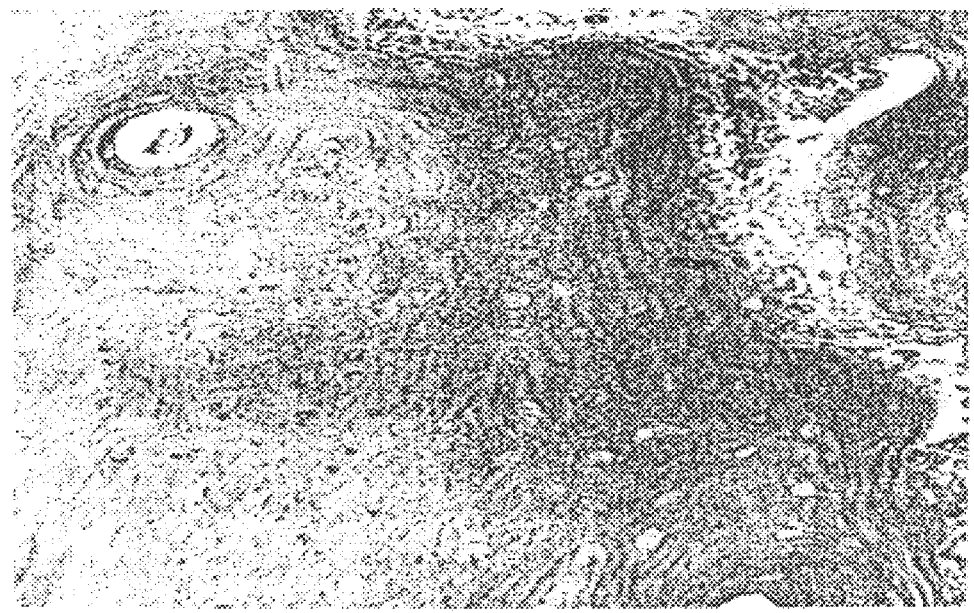
Figure 3D:
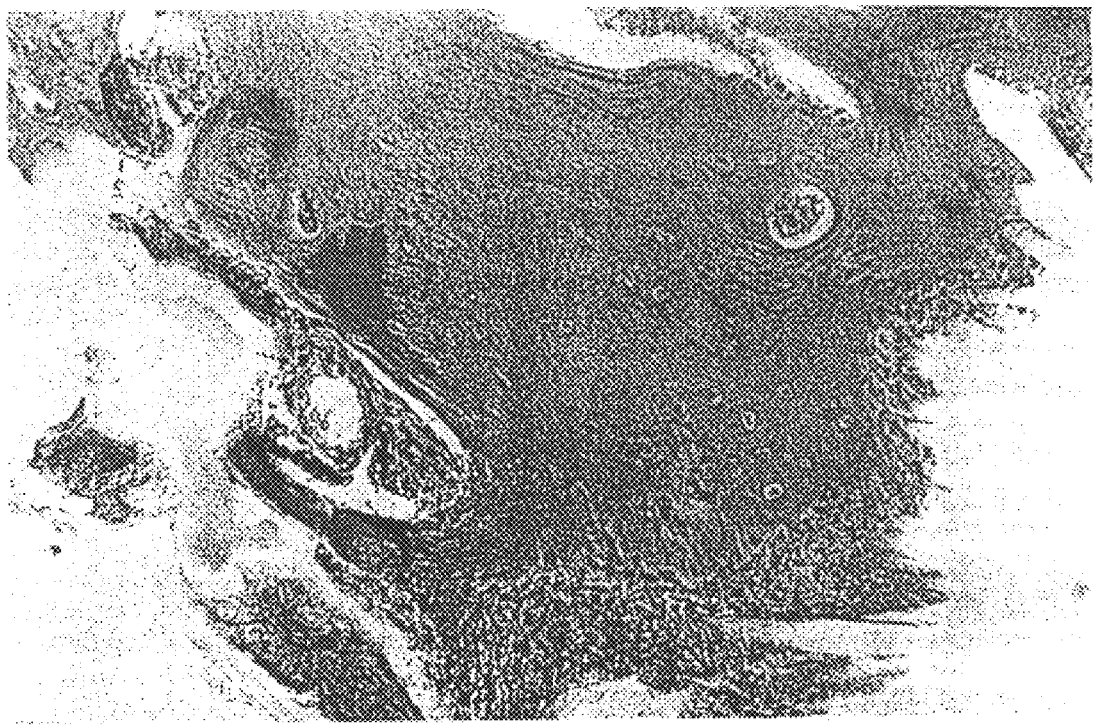

FIG. 2(a) shows tissue prepared as above kept in an incubator under static conditions (i.e. with no effects of rhythmic pressure). As can be seen the tissue is necrotic as evident by lysis of cells and spilling out of the nuclei to the medium. Against this FIG. 2(b) shows the same tissue kept in the system of the invention. The tissue remained viable with intact cells. These results show that the system of the invention is advantageous for maintaining viable tissue for prolonged periods of time.

EXAMPLE 2
Inducing Repair in Articular Defects.

Defects were created in vital articular cartilage explants which were placed in a system as described schematically in FIG. 1. The explants were grown and maintained in the system for 7–14 days to induce regeneration and repair in the tissue either by transplanting cells in adhesives or whole epiphyses. The results (not shown) indicate that cell and tissue integration and propagation within the defects took place signifying that the system of the invention enables repairment of defects in tissue and development of normal new tissue.

EXAMPLE 3
Scaffold Preparations From Soft and Calcified Connective Tissue Shunks Cortical and cancellous bone, articular, meniscal and tracheal cartilages all underwent basically the same chemical-enzymatic and mechanical procedure for their adjustment as a scaffold. The scaffolds were used for cell and tissue explant adherence and growth, in the process of in vitro reconstruction of composite engineered cartilaginous implants to induce regeneration and repair in damaged articular cartilages.

1. The tissue samples were cleaned of soft tissue residues and underwent three cycles of freezing and thawing using liquid nitrogen for freezing and double distillad water for thawing, followed by three washes in phosphate buffered saline (PBS) at pH 7.4, getting rid of the cytoplasmic content of the lysing cells.
2. The tissue samples were further extracted by constant stirring in 4M guanidinium chloride for 48 hours in the cold room. After thoroughly washes in $dH_2O$, removal of all chlorides was assessed using $AgNO_3$.
3. Calcified tissue further underwent a decalcification step by either EDTE, acids or special reagents, followed by thoroughly washes with distilled water and PBS.
4. For removing lipids the samples were extracted by constant stirring with chloroform:methanol (1:1 v/v) in the cold room, until no more yellowish substances were extractable. To remove the organic solvents the samples were washed with PBS for overnight under constant stirring in the cold.
5. A short collagenase digestion (37.5 units/ml) was performed for one hour in PBS at 37° C. The digestion was terminated and followed by rinsing twice in saline (0.9% NaCl).
6. The collagenase treatment was followed by a short papain further (proteolytic) digestion (25 µl Sigma concentrate/ml papain buffer (pH 5.4) containing cysteine (1 mg/ml)).
7. The samples were rinsed 5 times in saline enriched by antibiotics.
8. Production of pores was performed by hammering the tissue over a scraper and rinsing with PBS.
9. The tissue samples were kept sterile and frozen till it was collected for in vitro reconstruction with cells and tissue explants, designed for implantation.

Variation of this procedure is dependent on the exact consistency of the original tissue used.

EXAMPLE 4
Sugar Cross-linking of Matrix Agents Added to Natural Tissue to be Used as Scaffold One percent solutions of hyaluronic acid, cartilage proteoglycan-aggrecan, various glycosaminoglycans, (chondroitin sulfates, keratan sulfates, heparan sulfates (syndican and perlican), dextran sulfate (synthetic), egg lysozyme, polylysine (synthetic), arteparon ect., were mixed with either 1% ribose or 1% xylose in the cold in suspension with the treated tissue scaffold, for 3 days in the cold room. Then the tissue samples were washed thoroughly in PBS.

EXAMPLE 5
Implant Scaffolds Impregnated With Cells

Chondrocytes from human arthroscopic biopsies, were cultured to a cell density of $10^7$ cells/$cm^2$. Scaffold enriched with matrix constituents were formed from one of the following: (1) demineralized bone matrix; and (2) modified cross-linked small intestine submucosa.

Demineralized cortical and spongious bone was treated mechanically to produce porosity by hammering the tissue over a scrapper device.

Pig small intestine submucosa (SIS) deficient of its endothelial layer was modified by guanidinium chloride extraction, and sugar cross-linking as explained above. Hyaluronic acid and chemically altered hyaluronic acid molecules. The above human artheroscopic derived differentiated cultures were used as cell source for impregnating the scaffold.

Figure 4A:
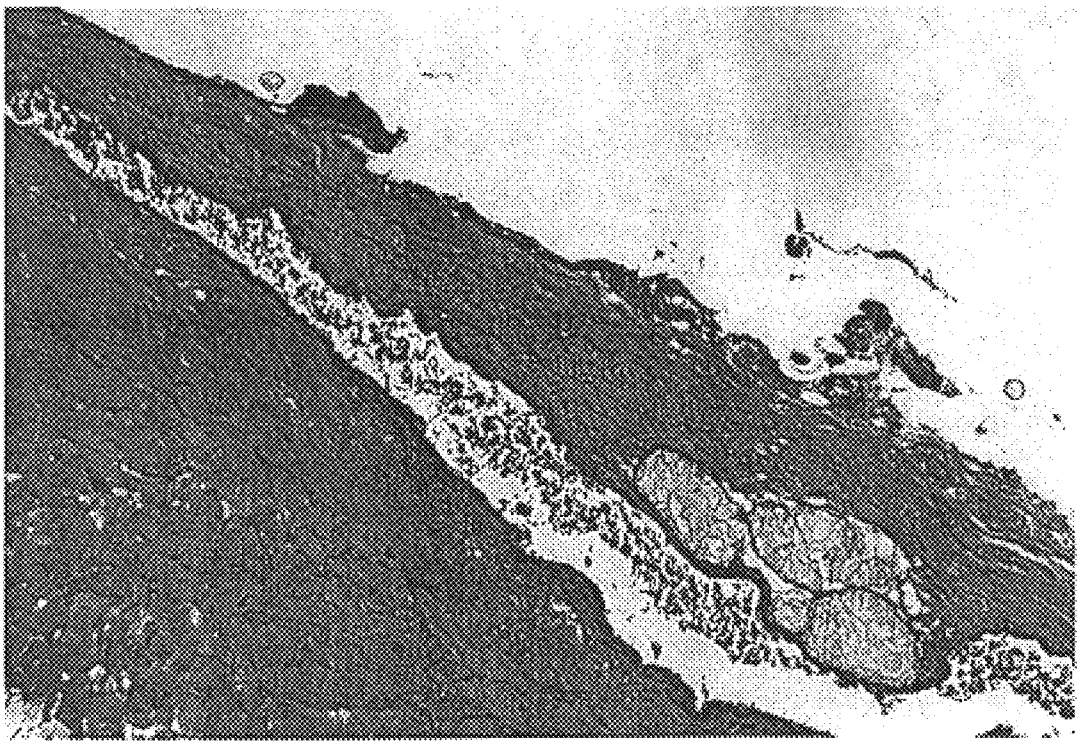
FIGS. 4(a)–(b) shows histological cross-sections of scaffolds of the invention composed of pig small intestine submucosa (SIS) modified by cross-linking, impregnated with human chondrocytes.
Figure 4B:
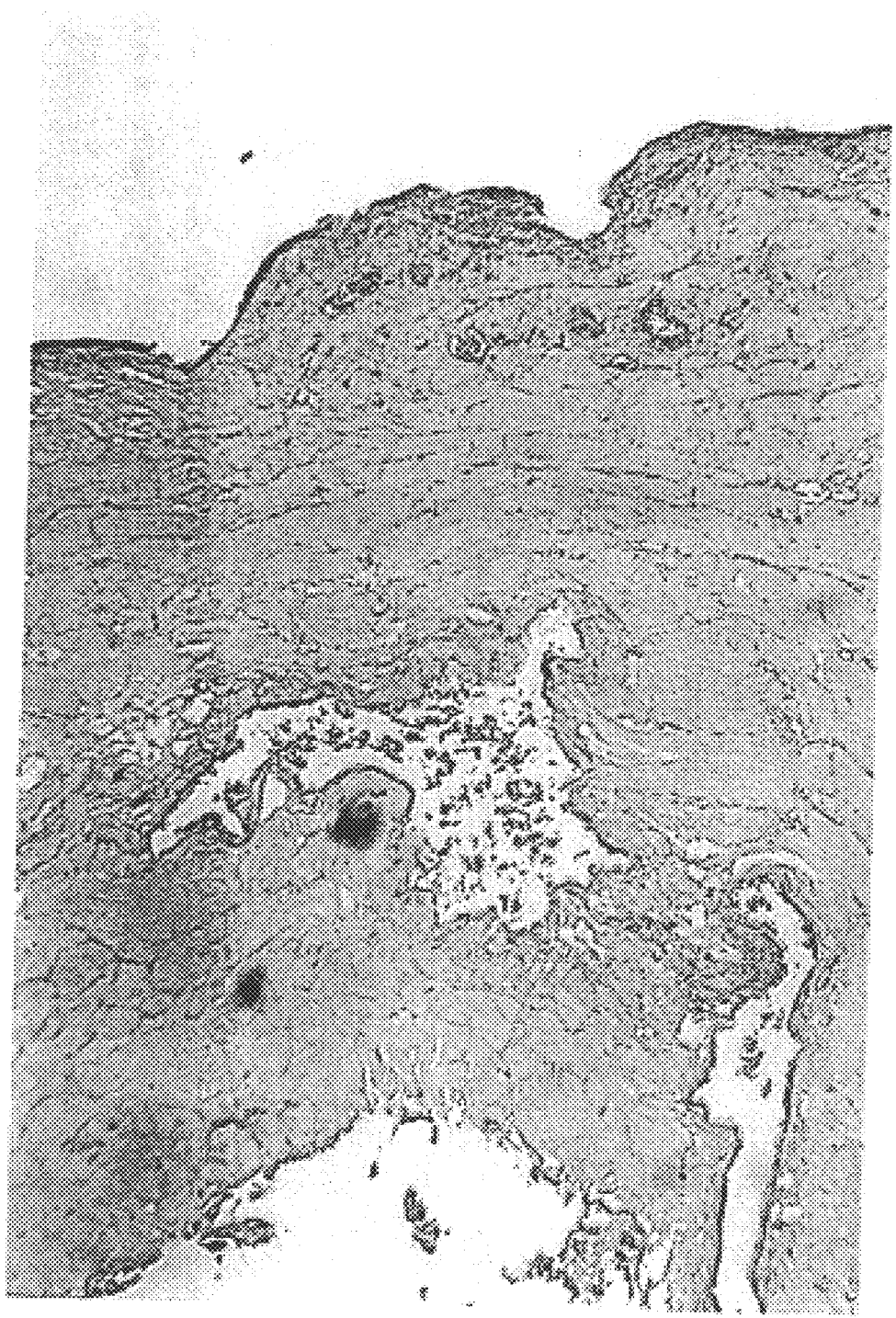

The results are shown in FIGS. 3($a$)–3($b$) which show several different histological preparation of demineralized cortical and spongious bovine bones impregnated in cells and in FIGS. 4($a$) and 4($b$) which show a pig small intestine submucosa (SIS) devoid of its endothelial layers modified by guanidinium chloride exaction and cross-linked as above.

As can be seen, both types of scaffolds of the invention supported maintenance of viable cells, show normal morphology.

EXAMPLE 6
Embryonal Epiphyses as Implants to Repair Articular Cartilage Defects With and Without Embedding in a Scaffold.

Fresh embryonal epiphyses were isolated and cleaned of soft tissues of long bones tibias and femurs of fetuses at medium gestation and up to birth (the younger gestation age the better). The isolated and cleaned epiphyses can be maintained vital for weeks, up to the need for implantation, under a constant perfusion in the system of the invention. The separated epiphyses tend under these cultured conditions to associate (fuse together) into one tissue piece. The vitality of the newly formed tissue compared to epiphyses maintained under regular static culture conditions was assessed by:

(a) Histology, histochemistry and immunohistochemical staining procedures,
(b) Incorporation of $^{35}$S-carrier free sulfate into isolated glycosaminoglycan macromolecules, and
(c) By XTT reagent measuring cell vitality in a standard tissue ring specimens by reduction of tetrazolium salts by the cell's mitochondrial hydrogenases, yielding a soluble colored molecule—a format dye, measured at 450 nm with an ELISA plate reader. The optical density is proportional to the number of living cells and their metabolic status.

These biological in vitro reconstructed (engineered) tissues have clear advantages as implants as follows:

a) The engineered in vitro reconstructed cartilaginous implants are readily malleable to fit the exact shape and size of the articular defects.
b) They are readily squeezed in and strongly held (anchored) into the lesion sites, integarating rapidly with the neighboring cartilage and bone tissues.

Figure 5:
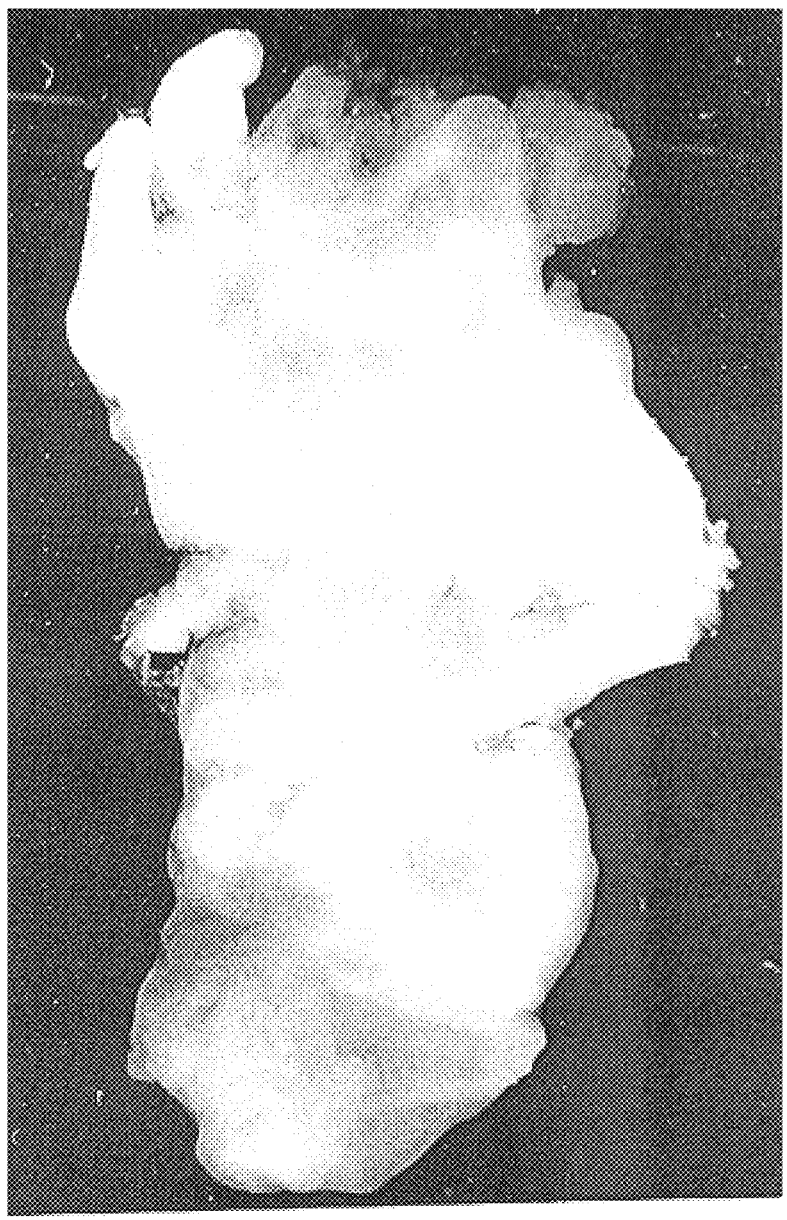
FIG. 5 shows epiphyseal tissue resulting from spontaneous fusion.
Figure 6:
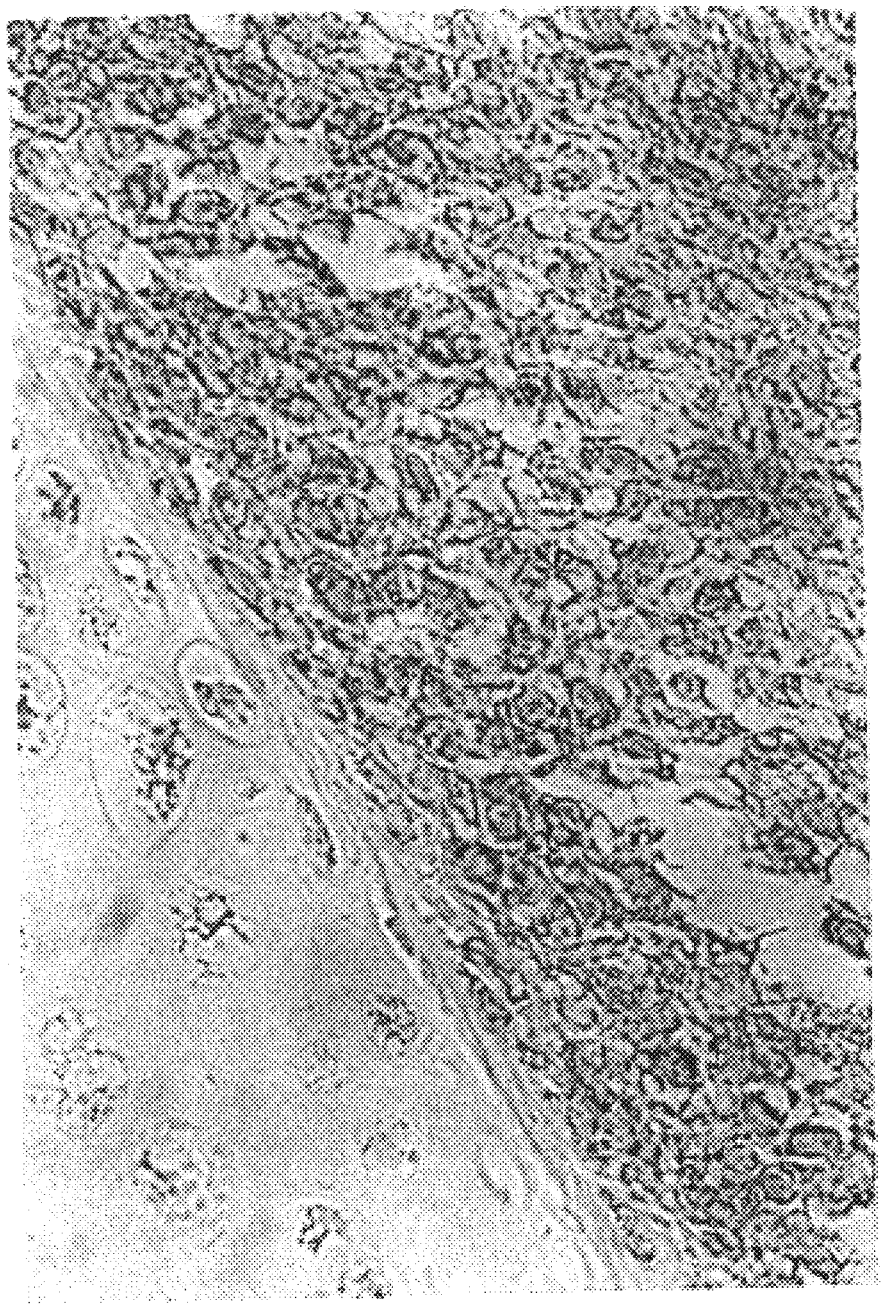
FIG. 6 shows a histological section of the tissue of FIG. 5.

FIG. 5 shows epiphyseal tissue which has been spontaneously fused, maintained and in the system of the invention demonstrates that the system of the invention can maintain relatively large pieces of tissue in viable state for extended periods of time. FIG. 6 shows a histological cross-section of the tissue of FIG. 5. As can be seen, the system of the invention supports the viability of a large range of different cells at a wide range of differentiated stages as evident from the fact that various stages of differentiation were maintained in a viable state.

What is claimed is:

1. A system for the maintenance of viable tissue comprising:
   (i) a chamber for holding the tissue, the chamber having in it an atmosphere, the composition of which is suitable for maintenance of viable biological tissue;
   (ii) means for maintaining the atmosphere at a substantially constant gas composition and for maintaining temperature at a substantially constant temperature;
   (iii) a reservoir for holding tissue culture medium, said reservoir being in flow communication with the chamber;
   (iv) a pump means for circulating the medium between the chamber and the reservoir in a controlled manner; and
   (v) control means for controlling the pump means to circulate the medium such that it produces rhythmic pulses of pressure on tissue in the chamber, said pressure being between 0.5 to 30 atm, and said rhythmic pulses having a frequency of 5–300 per minute.

2. The system of claim 1 in which said means for maintaining the atmosphere is an incubator.

3. A system according to claim 1, wherein the tissue is a three-dimensional tissue.

4. A system according to claim 1, wherein the frequency is 10–200 per min.

5. A system according to claim 4, wherein the frequency is 60–120 per min.

6. A system according to claim 1, wherein the pressure is 1 to 10 atm.

7. A system according to claim 6, wherein the pressure is 2 to 3 atm.

8. The system of claim 1, wherein the means for maintaining a substantially constant gas composition maintains the atmosphere at 5% to 10% $CO_2$ in air.

9. The system of claim 1, wherein the control means comprises a computer that controls timing and pausing of the pump means to produce said rhythmic pulses of pressure.

10. A system according to claim 1, wherein the control means controls the pump to change direction of flow of the medium between the chamber and the reservoir every 1 to 3 minutes.

* * * * *